United States Patent [19]

Ralls et al.

[11] Patent Number: 6,015,681
[45] Date of Patent: Jan. 18, 2000

[54] RAPID IMMUNOASSAY FOR CARIOGENIC BACTERIA

[75] Inventors: Stephen Alden Ralls, Great Lakes; Lloyd Grant Simonson, Spring Grove, both of Ill.

[73] Assignee: The United States of America as represented by the Secretary of the Navy, Washington, D.C.

[21] Appl. No.: 08/766,203

[22] Filed: Dec. 12, 1996

Related U.S. Application Data

[63] Continuation-in-part of application No. 08/508,653, Jul. 28, 1995, abandoned.

[51] Int. Cl.$^7$ .................. G01N 33/554; G01N 33/53; G01N 33/537; G01N 33/543
[52] U.S. Cl. .................. 435/7.32; 435/7.34; 435/7.9; 435/7.92; 435/35; 435/975; 436/518; 436/524; 436/530; 436/548
[58] Field of Search .................. 435/7.32, 7.34, 435/7.9, 7.92, 35, 975; 436/518, 524, 530, 548

[56] References Cited

U.S. PATENT DOCUMENTS 4,632,901  12/1986  Valkirs et al. .
5,017,342  5/1991  Haberzettl et al. .
5,103,836  4/1992  Goldstein et al. .

FOREIGN PATENT DOCUMENTS 496 345  7/1992  European Pat. Off. .

OTHER PUBLICATIONS

Kinet et al(Biochemistry vol. 24, pp. 4117–4124), 1985.

*Primary Examiner*—Anthony C. Caputa
*Assistant Examiner*—Mark Navarro
*Attorney, Agent, or Firm*—A. D. Spevack

[57] ABSTRACT

An assay method and kit for detecting specific oral cariogenic bacteria, e.g., mutans streptococci, Lactobacillus sp. and Actinomyces sp., separately or in combination, comprising gathering a sample suspected of containing cariogenic bacteria; treating the sample with a stripping buffer to remove host antibodies from bacteria present in the sample; retaining the treated bacteria on a blocked solid phase substrate; reacting the retained bacteria with a primary antibody specific for the desired cariogenic bacteria; reacting the primary antibody with a conjugated label producing a detectable signal; and detecting the signal whereby the presence of the desired cariogenic bacteria is determined in the sample. The device for conducting these assays is a frame or support which holds a solid substrate capable of retaining the bacteria of interest while permitting drainage of other materials or fluids away from the retained bacteria.

9 Claims, 1 Drawing Sheet

RAPID IMMUNOASSAY FOR CARIOGENIC BACTERIA

RELATED APPLICATION

This Application is a continuation-in-part of U.S. patent application Ser. No. 08/508,653 filed Jul. 28, 1995 now abandoned.

BACKGROUND OF THE INVENTION

1. Field of the Invention

This invention relates to an immunodiagnostic assay method and kit to rapidly detect oral cariogenic bacteria, i.e., mutans streptococci, Lactobacillus sp. and Actinomyces sp., in human dental plaque, saliva and oral rinse samples.

2. Description of the Prior Art

Certain species of oral bacteria have been associated with dental caries in humans (1). The presence of mutans streptococci, which includes *Streptococcus mutans* and *Streptococcus sobrinus,* is highly correlated with dental caries and this has been widely addressed in the dental literature (1–23). *Streptococcus mutans* is considered the foremost bacterial species associated with the development of human dental caries (12). Various serotypes (serovars) of *Streptococcus mutans* have been described (17). Lactobacillus sp. (2, 3, 13, 14, 18–24) and Actinomyces sp. (19, 23–26) have also been associated with human dental caries. Ebersole has described a SEROLOGICAL METHOD FOR THE IDENTIFICATION OF MICROORGANISMS in U.S. Pat. No. 4,458,014 specifically for the identification of diseases of the mouth. Chen et al. have described in U.S. Pat. No. 4,866,167 a DETECTION OF HUMAN ORAL CELLS BY NUCLEIC ACID HYBRIDIZATION to detect *Streptococcus mutans* and other bacterial species. The methods of both Ebersole and Chen et al. are technically complex, time consuming and are not rapid.

Toshitsugu et al. European patent 0 496 345 A1 have described a METHOD FOR DETECTING AND QUANTIFYING CARIOGENIC BACTERIA. There are several important differences between their invention and the invention described herein. Toshitsugu et al. do not strip off antibodies present on bacteria prior to reacting bacteria with antibodies. They disperse their sample containing *Streptococcus mutans* to "an optimal buffer solution suitable for the antigen-antibody reaction . . . " The invention described herein uses a buffer that is not suitable for the antigen-antibody reaction and, to the contrary, strips off antibodies from oral bacterial antigens. Toshitsugu et al. use conventional millipore membrane filters activated by vacuum (suction), centrifugation, or syringe pressure; the invention described herein uses a flow-through device which filters passively by gravity or wicking action. Filtration to Toshitsugu et al. means filtration under pressure using a syringe, suction/vacuum filtration, or centrifugation filtration; the invention described herein never uses any of those active types of filtration. Toshitsugu et al. have no negative control built into their system; they react the entire surface of the membrane filter. The invention described herein reacts in only a spot on the filter surface leaving the surrounding area as a negative control which is not possible with their test. Their test also does not exclude the possibility that the peroxidase they detect may be of human or microbial origin. The test of Toshitsugu et al. is not rapid. Their test always takes more than one hour—usually from 1 to 18 hours, or longer. The test specified in most of their examples takes over 2 hours; the test described herein can be performed in 5 minutes. Additionally, as mentioned in their example 4, they incubate twice at 37° for one hour for their antigen-antibody reaction and indirect labeling; the invention described herein never requires an incubator. In all their examples, they use a spectrophotometer to read color development in fluid; the test described herein never uses a spectrophotometer to read color development; in the test described herein color development is done visually against a standard and is not read in fluid. There are some other lesser differences, but nevertheless important between their patent and the one described herein. In some cases, they disperse the plaque sample by sonication as in their example 13; sonication is never used in the invention described herein.

Their filter is placed in a separate well for color development; the filter is not removed for color development with the invention described herein. Also in the invention described herein, polyclonal antibodies are absorbed to make them specific; Toshitsugu et al. make no mention of absorption and mention that specificity of polyclonal antibodies is a problem. Lastly, they have a filter membrane air drying step; the filter in the invention described herein is never dried in the air or removed for measurement.

The use of antisera to mutans streptococci, Lactobacillus sp. and Actinomyces sp., separately or in combination, has not been reported as part of a simple, rapid, chairside assay. The rapid detection of these cariogenic bacteria assists in the accurate diagnosis and prediction of active dental caries where other methods are limited and at a rate faster than now available through Chen et al., Ebersole or Rosenberg et al. U.S. Pat. No. 4,976,951, DENTAL CARIES DIAGNOSTIC AND LOCALIZATION TECHNIQUE.

Previous methods can detect *Streptococcus mutans* levels in 48 hours using dental plaque (U.S. Pat. No. 3,746,624) or saliva (Dentocult SM Strip Mutans, Vivacare diagnostic line/VIVADENT, manufactured by Orion Diagnostica, Espoo, Finland). These older methods are considered too slow, particularly by dentists seeking immediate answers for patients in their care and by persons who are traveling to distant locations where dental services are difficult to obtain. What is needed is a simple to operate assay to detect cariogenic bacteria that can be developed and read in less than an hour, requires no expensive equipment and can be performed preferably in five minutes or less.

SUMMARY OF THE INVENTION

Accordingly, an object of this invention is an immunodiagnostic assay method for rapidly detecting the presence of mutans streptococci, Lactobacillus sp. and Actinomyces sp., separately or in combination, in human dental plaque, saliva or oral rinse samples.

Another object of this invention is an assay method for rapidly assisting in the assessment of a patient's risk for developing dental caries.

A further object of this invention is an assay method for rapidly determining caries activity (positive for a certain level of cariogenic bacteria) of a dental defect suspected of being carious through clinical or radiographic examination, or through other means.

An additional object of this invention is a kit for conducting the rapid immunoassay.

These and additional objects of the invention are accomplished by an assay for detecting cariogenic bacteria, e.g., mutans streptococci, Lactobacillus sp. and Actinomyces sp., separately or in combination, comprising gathering a sample suspected of containing the oral bacteria of interest (target), using a stripping buffer to remove all host antibodies from the bacteria, immobilizing any oral bacteria present on a solid substrate, contacting the sample with polyclonal antibodies (absorbed animal antiserum) and/or monoclonal antibodies that are specific for the sought or target oral cariogenic bacteria, contacting the antibodies with a label or indicator capable of being detected thereby identifying the presence of the antibodies, and detecting the label, whereby the presence of the cariogenic bacteria in the sample is determined. The device for conducting these assays is a frame or support which holds a solid substrate capable of binding the sought antigens of interest (target) while permitting drainage of other materials or fluids away from the bound antigens.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

Figure 1B:
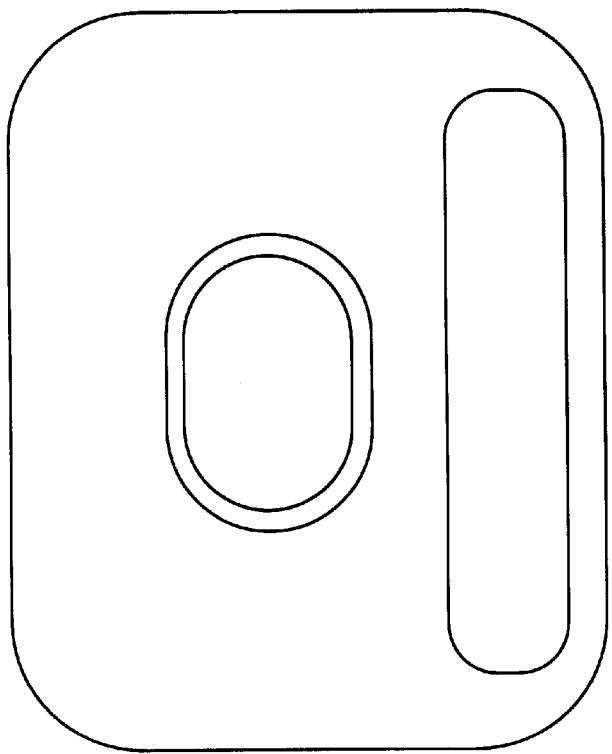
FIG. 1b is an embodiment of the device for the method and illustrates a negative reaction and the absence of *Streptococcus mutans*.

The invention is directed to immunodiagnostic assays to detect cariogenic oral bacteria. Within this invention, the term cariogenic bacteria encompasses Lactobacillus sp., Actinomyces sp. and all mutans streptococci including *Streptococcus mutans* and *Streptococcus sobrinus*. The presence of certain levels of mutans streptococci and Lactobacillus sp. normally indicates active carious dental lesions or an increased probability to develop such lesions. The invention relates to the detection of preferably mutans streptococci, including *Streptococcus mutans* and *Streptococcus sobrinus*, and also Lactobacillus sp. The invention also relates to the detection of Actinomyces sp. which have also been associated with dental caries. The invention would normally detect the different cariogenic bacteria separately, but they could be detected in combination. The invention can be used for site-specific applications, whole-mouth screening and as part of a risk assessment program. Polyclonal antibodies directed against the cariogenic bacteria can be incorporated into an immunodiagnostic to detect or predict active carious dental lesions from human dental plaque (site-specific), saliva (whole-mouth screening) or oral rinse (whole-mouth screening) samples. The antisera provide a source of antibodies suitable for rapid, chairside detection of oral cariogenic microbial antigens. This rapid assay method for determining the presence of cariogenic bacteria in oral clinical specimens is fully developed and readable in under an hour, usually about five minutes or less. Within this invention, the term rapid assay is an assay or test that can be developed in under an hour, preferably in less than one-half hour. Most preferably, this assay is fully readable in approximately five minutes or less from the application of the patient's dental plaque, saliva or oral rinse sample to the device. The method and equipment are technically easy to use.

Oral cariogenic infections pose a serious oral health problem. This invention will rapidly determine whether a specific dental defect which is noted on clinical or radiographic examination, or through other means, is an active carious lesion (positive for a certain quantitative level of cariogenic bacteria). This invention will also allow the screening of patients for active carious dental lesions and also help identify patients who are at highest risk for developing dental caries. The invention is planned as a cornerstone of an institutional caries risk assessment program. The value of this invention in a risk assessment program is that by knowing caries risk, treatment resources can be directed in the most effective and efficient manner. The primary advantage of this assay method is that it can be performed and read in about five minutes compared to 48 hours or longer required for the earlier tests. The method is technically simple, sensitive, specific and semi-quantitative. The method can be used in a dental operatory with definitive results obtained while the patient is still in the chair, thus allowing treatment decisions to be made more rapidly.

In general, polyclonal or monoclonal antibodies are prepared in rabbits although other animals can be used. Antibodies are naturally produced biomolecules which react specifically with other foreign biomolecules called antigens. Antibodies are created by immunizing an animal, preferably in this case rabbits, with killed cariogenic bacteria. A process such as described by Ebersole in U.S. Pat. No. 4,458,014 can be used to prepare the antibodies. This immunization causes the rabbits to produce antibodies that are directed against these bacteria (17). In purified form, these antibodies are used as reagents to aid in the rapid detection of the bacteria and early diagnosis or prediction of active dental caries in humans.

In general, the invention is a clinical diagnostic method using polyclonal antibodies directly or indirectly to detect the presence of cariogenic bacteria by a detectable label. The method comprises gathering a sample suspected of containing the oral bacteria of interest (target) from a patient. The sample can be gathered from patients by any of the known techniques for gathering dental plaque, saliva or oral rinse samples. Samples are generally incorporated into suitable sample media. An aliquot of the sample media is placed on a solid substrate, preferably a flow-through filter type device (such as marketed by Devaron, Inc., Dayton, N.J.) or a device such as described by Oprandy in U.S. Pat. No. 5,039,493. The oral bacteria present on the substrate are immobilized and the substrate blocked and washed. The substrate can be any of the commonly used substrates such as nitrocellulose filter media or any of the materials described by Oprandy. Once the unknown sample is immobilized on the substrate, the sample is contacted with previously prepared antibodies that are specific for the sought or target cariogenic bacteria (e.g., mutans streptococci). The antibodies are prepared by known means as described by Ebersole supra or others. The antibodies are contacted with a label capable of being detected, thereby identifying the presence of the antibodies. Any detectable label or indicator can be used such as enzymes (e.g., alkaline phosphatase; peroxidase; galactosidase; etc.) which react with their substrates to yield an insoluble end product. Labels such as colloidal gold coupled to protein-A, protein-G, or some other protein can also be used. Other suitable detectable labels include fluorescent markers, radionuclides, latex particles and others. Once labeled, the amount of the target cariogenic bacteria in the sample can be semi-quantified by detecting the relative strength of the color development produced by the labeling process.

Alternative embodiments can use monoclonal antibodies to the cariogenic bacteria instead of polyclonal rabbit sera. Additionally, the primary antibody can be conjugated with a label directly bypassing the need for a second conjugate label or secondary antibody. Also, the use of colloidal gold or other labels such as enzymes or fluorochromes can be attached to several probes such as protein-A, protein-G, goat anti-rabbit IgG, goat anti-mouse IgG, and others. Amplification of results can also be achieved by the well known biotin-avidin method.

In an additional alternative embodiment site specific plaque samples are assayed to assess levels of cariogenic bacteria at sites within a mouth. A site specific assay can be accomplished by pre-flossing the interproximal contact area of interest, placing a paper point (or floss section) just below the contact area, and adding a small amount of an appropriate buffer solution to the contact. The buffer solution will penetrate cavitated carious lesions and bacteria will be wicked with the buffer solution into the paper point. The paper point can then be tested using the general procedures in the example to follow.

Having described the invention, the following example is given to illustrate specific applications of the invention for *Streptococcus mutans*, including the best mode now known to perform the invention. The test can be configured to detect other mutans streptococci, Lactobacillus sp. and Actinomyces sp. primarily by substituting the primary antibody specified in step (e) below. This specific example is not intended to limit the scope of the invention described in this application.

EXAMPLE 1

An immunoassay to rapidly detect mutans streptococci, more specifically *Streptococcus mutans*, is described as follows:

(a) A clinical specimen of human saliva suspected of containing the bacteria of interest (*Streptococcus mutans* bacterial cells) is collected by having a patient masticate chewing gum for 30 seconds after which the patient expectorates their saliva into a small (30 ml) specimen cup.

(b) Three drops (150 µl) of the saliva are removed from the specimen cup with a bulb dropper and placed into a small (1.7 ml) sample vial. Three drops (150 µl) of an antibody stripping buffer are then added to the vial. The stripping buffer consists of MonoPure Elution Buffer (cat. no. 1851520, lot no. 870127087, Pierce Chemical Co., Rockford, Ill.) with 1% Tween-20 (no. 170-6531, Bio-Rad Labs) which is mixed 1:1 with 2 M sodium acetate buffer, pH 8.0. Mixing is completed by closing the cover on the sample vial and shaking vigorously.

(c) One drop (5 µl) of the saliva-stripping buffer solution of step (b) is spotted onto a pre-blocked, flow-through filter device (Devaron, Inc., Dayton, N.J., 0.45 µm) using a pipette or similar device. The solution is allowed to flow through completely, usually within 10 seconds. The flow-through filter device is pre-blocked to prevent nonspecific binding using a blocking solution of 0.05% gelatin (catalog no. G-8, 275 Bloom; lot no. 734286, Type A purified grade CAS reg. 9000-70-8, Fisher Scientific Co.) plus 0.05% skim milk, dehydrated (Difco, no. 0032-01, control no. 704524) in phosphate buffered saline (PBS). The blocking solution is heated to 56° C. overnight (about 18 hours). PBS, pH 7.4, 1 L, is prepared as follows:

| PBS, pH 7.4 | 1 L |
|---|---|
| Distilled water | 1000 ml |
| NaCl | 8.0 g |
| $KH_2PO_4$ | 0.2 g |
| $Na_2HPO_4 \cdot 12H_2O$ | 2.9 g |
| KCl | 0.2 g |
| $NaN_3$ | 0.2 g |

(d) The filter surface of the flow-through filter device is washed and blocked with 1 drop (50 µl) of a solution made by adding 0.05% Tween-20 (no. 170-6531, Bio-Rad Labs) to the blocking solution described in step (c) above (i.e., 0.5 ml/L). The washing solution is allowed to flow through the filter.

(e) One drop (50 µl) of specific protein-A affinity purified and absorbed polyclonal rabbit IgG to *Streptococcus mutans* (primary antibody) is then added to the filter surface of the flow-through filter device and allowed to flow through. The antibody is rabbit IgG to *Streptococcus mutans* which has been affinity purified using a Protein-A membrane affinity separation device (MASS-Nygene). The test can also be configured to detect other mutans streptococci, Lactobacillus sp. and Actinomyces sp. by substituting another appropriate primary antibody in this step.

(f) The filter surface of the flow-though filter device surface is washed and blocked as in step (d).

(g) One drop of a conjugated label (secondary antibody) is then added to the filter surface of the flow-through filter device and allowed to flow through. The conjugated label is prepared from goat anti-rabbit IgG (human antibody absorbed; heavy & light chains)-alkaline phosphatase labeled (cat. no. 62-6122, lot no. 50424642, Zymed Laboratories, Inc.) which is diluted 1:8 in PBS then 1:4 with Stabilzyme AP (cat. no. SA01-0125, lot no. SA01401, BSI Corp. Eden Prairie, Minn.) for a final 1:32 working dilution.

(h) The filter surface of the flow-through filter device surface is washed and blocked as in step (d).

(i) One drop of a liquid substrate is then added to the filter surface of the flow-through filter device and allowed to flow through. The liquid substrate is prepared from BCIP/NBT alkaline phosphatase substrate (5-bromo-4-chloro-3-indoxyl phosphate/p-nitroblue tetrazolium system)(cat. no. ES006-500 ml, Chemicon International Inc.) to which 0.5 mg Levamisole/ml (cat. no. L-9756; Sigma Chemical Co., St. Louis, Mo.) has been added. When positive for the desired species (or genus) of bacteria, a color develops which varies in intensity with the amount of antigen present on the surface of the filter device. An example of color development which is positive for the presence of *Streptococcus mutans* is presented in FIG. 1a. An example of a negative reaction to *Streptococcus mutans* is presented in FIG. 1b. The assay is usually completed in five minutes or less.

(j) Optionally, the reaction can be stopped or minimized using a reaction stopper solution composed of a 1:1 volume:volume mixture of 0.1 M EDTA (no. 4653, J.T. Baker Chemical Co., Phillipsburg, N.J.) with tris buffered saline, pH 2.8. The final pH=5.17 and the final EDTA=0.05 M. If used, two drops (100 µl) of the reaction stopper are applied to the filter surface and allowed to flow through.

Antibody production

New Zealand white rabbits were used for the development of the antibodies in the serum using a protocol similar to that described by Ebersole supra or others. The New Zealand white rabbits were male, approximately one year of age, and weighed approximately 9 to 10 pounds each. The serological production of antibodies in a rabbit system is a common and well-documented procedure. Many suitable established protocols are recorded in the scientific literature. The immunization protocol recommended by Ribi Immunochem Research, Inc. was used for the present example. Antibodies to specific mutans streptococci, e.g., *Streptococcus mutans* and *Streptococcus sobrinus* are not commercially available.
Test bleeding After 10 days from the booster injection, approximately 1–5 mls of whole blood were collected from each rabbit from a marginal vein of the ear to verify the antibody titer.
Terminal blood collection Acceptable titered blood was collected by cardiac puncture and the serum separated. Serum was centrifuged at 10,000×g and the supernatant was preserved by the addition of 0.1% sodium azide.
Absorption and affinity purification of antisera The antiserum was made specific for *Streptococcus mutans* by absorption with washed microbial antigens. First the antiserum was affinity purified by using a pleated capsule recombinant protein-A affinity device (MASS, Nygene Corp., Yonkers, N.Y.). This membrane affinity purification results in relatively pure IgG. For each 1 ml of rabbit IgG solution, 100 mg wet weight of formalin-fixed washed whole cells of *Streptococcus gordonii* ATCC 10558 were mixed and incubated with shaking at 37° C. for one hour followed by incubation for 12 hours at 4° C. The absorbed antiserum was centrifuged at 16,000×g for 60 minutes. The procedure was repeated using the following microbial antigens: *Streptococcus mutans* isolates AHT, BHT, and *Streptococcus sobrinus* isolates 6715-13 and SL-1. The absorbed antiserum was the specific anti-*Streptococcus mutans* reagent used in the present prototype immunoassay system.

EXAMPLE 2

An immunoassay to rapidly detect Lactobacillus sp. is described as follows:

(a) A clinical specimen of human saliva suspected of containing the bacteria of interest (Lactobacillus sp. bacterial cells) is collected by having a patient masticate chewing gum for 30 seconds after which the patient expectorates their saliva into a small (30 ml) specimen cup.

(b) Three drops (150 $\mu$l) of the saliva are removed from the specimen cup with a bulb dropper and placed into a small (1.7 ml) sample vial. Three drops (150 $\mu$l) of an antibody stripping buffer are then added to the vial. The stripping buffer consists of MonoPure Elution Buffer (cat. no. 1851520, lot no. 870127087, Pierce Chemical Co., Rockford, Ill.) with 1% Tween-20 (no. 170-6531, Bio-Rad Labs) which is mixed 1:1 with 2 M sodium acetate buffer, pH 8.0. Mixing is completed by closing the cover on the sample vial and shaking vigorously.

(c) One drop (5 $\mu$l) of the saliva-stripping buffer solution of step (b) is spotted onto a preblocked, flow-through filter device (Devaron, Inc., Dayton, N.J., 0.45 $\mu$m) using a pipette or similar device. The solution is allowed to flow through completely, usually within 10 seconds. The flow-through filter device is pre-blocked to prevent nonspecific binding using a blocking solution of 0.05% gelatin (catalog no. G-8, 275 Bloom; lot no. 734286, Type A purified grade CAS reg. 9000-70-8, Fisher Scientific Co.) plus 0.05% skim milk, dehydrated (Difco, no. 0032-01, control no. 704524) in phosphate buffered saline (PBS). The blocking solution is heated to 56° C. overnight (about 18 hours). PBS, pH 7.4, 1 L, is prepared according to step (c) of Example 1.

(d) The filter surface of the flow-through filter device is washed and blocked with 1 drop (50 $\mu$l) of a solution made by adding 0.05% Tween-20 (no. 170-6531, Bio-Rad Labs) to the blocking solution described in step (c) above (i.e., 0.5 ml/L). The washing solution is allowed to flow through the filter.

(e) One drop (50 $\mu$l) of specific protein-A affinity purified and absorbed polyclonal rabbit IgG to Lactobacillus sp. (primary antibody) is then added to the filter surface of the flow-through filter device and allowed to flow through. The antibody is rabbit IgG to Lactobacillus sp. which has been affinity purified using a Protein-A membrane affinity separation device (MASS-Nygene).

(f) The filter surface of the flow-though filter device surface is washed and blocked as in step (d).

(g) One drop of a conjugated label (secondary antibody) is then added to the filter surface of the flow-through filter device and allowed to flow through. The conjugated label is prepared from goat anti-rabbit IgG (human antibody absorbed; heavy & light chains)-alkaline phosphatase labeled (cat. no. 62-6122, lot no. 50424642, Zymed Laboratories, Inc.) which is diluted 1:8 in PBS then 1:4 with Stabilzyme AP (cat. no. SA01-0125, lot no. SA01401, BSI Corp. Eden Prairie, Minn.) for a final 1:32 working dilution.

(h) The filter surface of the flow-through filter device surface is washed and blocked as in step (d).

(i) One drop of a liquid substrate is then added to the filter surface of the flow-through filter device and allowed to flow through. The liquid substrate is prepared from BCIP/NBT alkaline phosphatase substrate (5-bromo-4-chloro-3-indoxyl phosphate/p-nitroblue tetrazolium system)(cat. no. ES006-500 ml, Chemicon International Inc.) to which 0.5 mg Levamisole/ml (cat. no. L-9756; Sigma Chemical Co., St. Louis, Mo.) has been added. When positive for the desired species (or genus) of bacteria, a color develops which varies in intensity with the amount of antigen present on the surface of the filter device. An example of color development which is positive for the presence of Lactobacillus sp. is identical in appearance to the positive result for *Streptococcus mutans* presented in FIG. 1a. An example of a negative reaction to Lactobacillus sp. is similarly identical in appearance to the negative result for *Streptococcus mutans* presented in FIG. 1b. The assay is usually completed in five minutes or less.

(j) Optionally, the reaction can be stopped or minimized using a reaction stopper solution composed of a 1:1 volume:volume mixture of 0.1 M EDTA (no. 4653, J.T. Baker Chemical Co., Phillipsburg, N.J.) with tris buffered saline, pH 2.8. The final pH=5.17 and the final EDTA=0.05 M. If used, two drops (100 $\mu$l) of the reaction stopper are applied to the filter surface and allowed to flow through.

Antibodies to Lactobacillus sp. were produced in a manner similar to that described for *Streptococcus mutans* in Example 1. Antisera for Lactobacillus sp. were absorbed and purified in a manner similar to that described for *Streptococcus mutans* in Example 1.

Figure 1A:
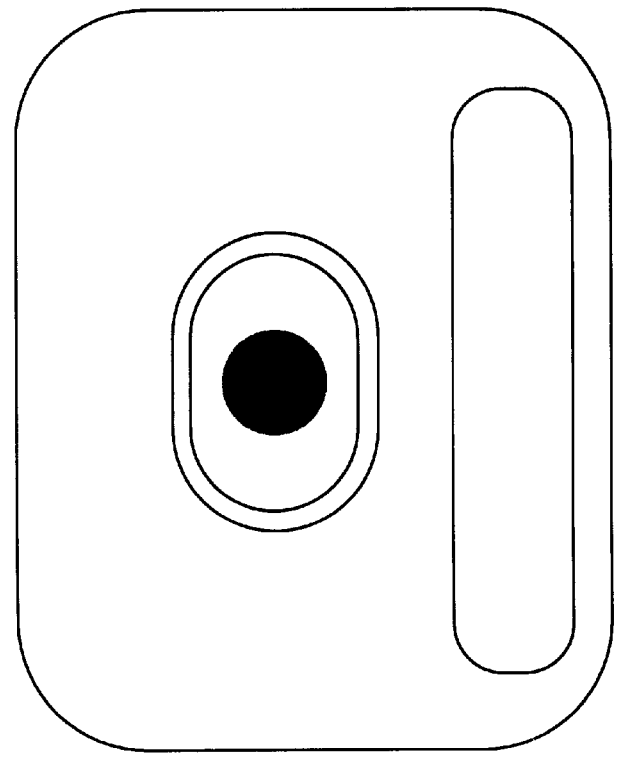
FIG. 1a is an embodiment of the device for the method and illustrates a positive reaction and the presence of *Streptococcus mutans*.

The assay does not have to be conducted in the particular order between immobilizing the antibody and antigen. In a preferred commercial embodiment, the known antibodies are immobilized on a solid substrate, preferably nitrocellulose media which is part of a flow-through filter device or similar. The device is then packaged until needed, preferably with the materials, reagents and instructions necessary to perform the assay. When needed, the device is removed from the packaging and a suspected antigen-containing sample is placed on the antibody-containing substrate surface. The substrate surface is then blocked and washed. An antibody label or indicator which reacts with the target bacterial antigens is then applied. When the conjugated label is alkaline phosphatase in the presence of a BCIP/NBT substrate system, a color will develop as shown in FIG. 1a for samples positive for certain levels of *Streptococcus mutans*.

ADVANTAGES AND NEW FEATURES

The invention can be used to evaluate site-specific areas of concern for caries activity, as a dental caries screening device and to assist in the assessment of a patient's overall risk for developing caries. The primary advantage of this assay method is that it can be performed and read in about five minutes compared to 1–48 hours required for the earlier tests. The method is technically simple to perform, sensitive, specific and semi-quantitative. The method can be used in a dental operatory with definitive results obtained while the patient is still in the chair, thus allowing more rapid treatment decisions to be made.

PUBLICATIONS

1. Shklair, I. L., Keene, H. J. and Simonson, L. G. Distribution and frequency of *Streptococcus mutans* in caries-active individuals. *J. Dent. Res.* 51(3):882, 1972.

2. van Houte, J. Role of microorganisms in caries etiology. *J. Dent. Res.* 73(3):672–681, 1994.

3. van Houte, J. Microbiological predictors of caries risk. *Adv. Dent. Res.* 7(2):87–96, 1993.

4. Marsh, P. D. Antimicrobial strategies in the prevention of dental caries. *Caries Res.* 27(suppl. 1):72–76, 1993.

5. Kuramitsu, H. K. Virulence factors of mutans streptococci: role of molecular genetics. *Crit. Rev. Oral. Biol. Med.* 4(2): 159–176, 1993.

6. Anderson, M. H. Changing paradigms in caries management. *Curr. Opin. Dent.* 2:157–162, 1992.

7. Suhonen, J. Mutans streptococci and their specific oral target. New implications to prevent dental caries? *Schweiz. Monatsschr. Zahnmed.* 102(3):286–291, 1992.

8. Bratthall, D. Mutans streptococci—dental, oral and global aspects. *J. Indian Soc. Pedod. Prev. Dent.* 9(1):4–12, 1991.

9. Tenovuo, J. and Aaltonen, A. S. Antibody responses to mutans streptococci in children. *Proc. Finn. Dent. Soc.* 87(4):449–461, 1991.

10. Alaluusua, S. Transmission of mutans streptococci. *Proc. Finn. Dent. Soc.* 87(4):443–447, 1991.

11. James, S. M. and Tagg, J. R. The prevention of dental caries by BLIS-mediated inhibition of mutans streptococci. *N.Z. Dent. J.* 87(389):80–83, 1991.

12. Jacobson, G. R., Lodge, J., and Poy, F. Carbohydrate uptake in the oral pathogen *Streptococcus mutans*: mechanisms and regulation by protein phosphorylation. *Biochimie.* 71(9–10):997–1004, 1989.

13. Krasse, B. Specific microorganisms and dental caries in children. *Pediatrician.* 16(3–4):156–160, 1989.

14. Krasse, B. Biological factors as indicators of future caries. *Int. Dent. J.* 38(4):219225, 1988.

15. Hamada, S. and Slade, H. D. Biology, immunology, and cariogenicity of *Streptococcus mutans*. *Microbiol. Rev.* 44(2):331–384, 1980.

16. Rogers, A. H. Immunization against dental caries: a review. *Aust. Dent. J.* 27(2):81–85, 1982.

17. Perch, B., Kjems, E., and Ravn, T. Biochemical and serological properties of *Streptococcus mutans* from various human and animal sources. *Acta Path. Microbiol. Scand.* Section B 82:327–340, 1974.

18. Ellen, R. P., Banting, D. W., and Fillery, E. D. *Streptococcus mutans* and Lactobacillus detection in the assessment of dental root surface caries risk. *J. Dent. Res.* 64(10):1245–1249, 1985.

19. Meiers, J. C., Wirthlin, M. R., and Shklair, I. L. A microbiological analysis of human early carious and non-carious fissures. *J. Dent. Res.* 61(3):460–464, 1982.

20. Arneberg, P., Ögaard, B., Scheie, A.Aa., and Rölla, G. Selection of *Streptococcus mutans* and lactobacilli in an intra-oral human caries model. *J. Dent. Res.* 63(10):1197–1200, 1984.

21. Duchin, J. L. and van Houte, J. Relationship of *Streptococcus mutans* and lactobacilli to incipient smooth surface dental caries in man. *Arch. Oral Biol.* 23:779–786, 1978.

22. van Houte J. and Green, D. B. Relationship between the concentration of bacteria in saliva and the colonization of teeth in humans. *Infect. Immun.* 9:624–630, 1974.

23. Bowden, G. H. W. Microbiology of root surface caries in humans. *J. Dent. Res.* 69(5):1205–1210, 1990.

24. Shovlin, F. E. and Gillis, R. Biochemical and antigenic studies of lactobacilli isolated from deep dentinal caries. I. Biochemical aspects. *J. Dent. Res.* 48:356–360, 1969.

25. Batty, I. *Actinomyces odontolyticus*, a new species of actinomyces isolated from deep carious dentine. *J. Pathol. Bact.* 75:455–459, 1958.

26. Nyvad, B. and Kilian, M. Microflora associated with experimental root surface caries in humans. *Infect. Immun.* 58(6):1628–1633, 1990.

Obviously, many modifications and variations of the present invention are possible in light of the above teaching. It is therefore to be understood that, within the scope of the appended claims, the invention may be practiced otherwise than as specifically described. The principles described above can be readily modified or adapted for various applications without departing from the generic concept, and therefore such adaptations and modifications are intended to be comprehended within the meaning and range of equivalents of the enclosed embodiments. It is to be understood that the terminology and phraseology herein is for the purpose of description and not of limitation.

What is claimed is:

1. A method for semiquantitatively detecting, in less than 30 minutes, a predesignated, target cariogenic bacteria in a sample selected from the group consisting of human dental plaque, saliva, and oral rinse which comprises the following steps:

(a) treating the sample with a antibody stripping buffer that removes all host antibodies from any target cariogenic bacteria present in the sample and said buffer does not support an antigen/antibody interaction;

(b) spotting onto and filtering the stripping buffer treated bacteria suspension or solution through a blocked solid phase substrate thereby retaining the treated target bacteria in a spot on the blocked solid phase substrate;

(c) reacting the retained treated target bacteria spot with a primary antibody specific for the target cariogenic bacteria;

(d) previously, simultaneously or subsequently to said primary antibody reacting with the target cariogenic bacteria reacting the primary antibody with a conjugated label producing a detectable signal; and (e) detecting the signal whereby the presence of the target bacteria is determined in the sample by the intensity of the signal.

2. The method of claim 1 wherein the conjugated label is selected from the group consisting of a label conjugated to a secondary antibody specific for the primary antibody, a label conjugated to Protein A, and a label conjugated to Protein G.

3. The method of claim 2 wherein the label is selected from the group consisting of colloidal gold, enzymes, fluorescent markers, radionuclides, and latex particles.

4. The method of claim 2 wherein the conjugated label is selected from the group of enzymes consisting of alkaline phosphatase, peroxidase, galactosidase, glucose oxidase, and urease.

5. The method of claim 1 wherein the primary antibody is labeled before it is contacted with the treated, target bacteria.

6. The method of claim 1 wherein the cariogenic bacteria are selected from the group consisting of mutans streptococci, Lactobacillus sp. and Actinomyces sp.

7. A kit for semi-quantitatively detecting cariogenic bacteria in human dental plaque, saliva, and oral rinse samples comprising:
 (i) a blocked solid phase substrate;
 (ii) antibody stripping buffer which removes all host antibodies from sample bacteria;
 (iii) a primary antibody that specifically reacts with the cariogenic bacteria; and
 (iv) a conjugated label.

8. The kit of claim 7 wherein the conjugated label is an enzyme conjugated to a secondary antibody specific for the primary antibody and the kit further comprises a substrate to enzymatically react with an enzyme-labeled secondary antibody.

9. The kit of claim 7 wherein the primary antibody is directly labeled.

\* \* \* \* \*